US00PP32026P2

(12) United States Plant Patent
Hansen

(10) Patent No.: US PP32,026 P2
(45) Date of Patent: Jul. 28, 2020

(54) ***GERANIUM* PLANT NAMED 'BOOM CHOCOLATTA'**

(50) Latin Name: ***Geranium* hybrid**
Varietal Denomination: Boom Chocolatta

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,923

(22) Filed: Feb. 1, 2019

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./324
CPC ..... A01H 5/02; A01H 5/0277; A01H 5/00; A01H 6/42; A01H 6/425
See application file for complete search history.

(56) References Cited

PUBLICATIONS

Hillen Nursery 2019 retrieved on Oct. 3, 2019, retrieved from the Internet at http://secureservercdn.net/72.167.241.180/be4.33b.myftpupload.com/wp-content/uploads/2018/11/2019-Catalogue.pdf, 3 cover page, pp. 1-3,7,23,last cover page or 9 total pages. (Year: 2019).*

* cited by examiner

*Primary Examiner* — June Hwu

(57) ABSTRACT

The new and distinct hybrid of Hardy *Geranium* plant named *Geranium* 'Boom Chocolatta' with large, rounded, deeply-cleft, palmately-lobed foliage having dark bronze color. Numerous, densely-branched, erect, stems display blue-purple flowers above the foliage beginning early summer for about three weeks. The new plant is vigorous and produces large, upright, winter-hardy mounds.

1 Drawing Sheet

Botanical denomination: *Geranium* hybrid.
Variety denomination: 'Boom Chocolatta'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2018. The claimed plant was first sold on Aug. 20, 2018 by Walters Gardens, Inc., who obtained the plant and all information relating thereto, from the inventor. No plants of *Geranium* 'Boom Chocolatta' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Hardy *Geranium* in the Geraniaceae family and given the cultivar name of 'Boom Chocolatta'. *Geranium* 'Boom Chocolatta' was hybridized by the inventor on Jun. 7, 2012 at a wholesale perennial nursery in Zeeland, Mich., USA. The seed or female parent was *Geranium pratense* 'Midnight Blues' U.S. Plant Pat. No. 22,455 and the pollen or male parent was presumed to be *Geranium clarkei* 'Kashmir Blue'. Seeds resulting from this cross were sown Aug. 9, 2012 at the same nursery.

*Geranium* 'Boom Chocolatta' was first selected in the summer of 2014 and assigned the breeder code 12-47-3 through the final evaluation process in the summer of 2016 when it was selected from among many other seedlings from the same cross and hundreds of other crosses. *Geranium* 'Boom Chocolatta' has been asexually propagated by shoot tip cuttings at the same nursery in Zeeland, Mich. in fall of 2014 initially by division and later shoot-tip, tissue culture propagation, and the resultant plants have remained stable and continued to exhibit the same characteristics as the original plant for multiple generations.

BRIEF SUMMARY OF THE INVENTION

The nearest comparison varieties include: the seed cultivar 'Midnight Reiter' (not patented) and 'Dark Reiter' (not patented). 'Midnight Reiter' seedlings are less robust, slower growing and has darker foliage than the new plant. 'Dark Reiter' is slower growing, smaller in habit and has darker foliage. 'Midnight Blues' is smaller in habit and leaf, less vigorous than the new plant and has darker grey-purple foliage and flowers of a different hue.

*Geranium* 'Boom Chocolatta' differs from its parents as well as all other Hardy *Geranium* known to the applicant in the following combined traits:

1. The large foliage is rounded, dark-bronze, deeply-cleft, palmately-lobed;
2. Winter-hardy, perennial, upright mounded habit.
3. Flowers have medium blue-purple petals with reddish-purple veins;
4. Growth is vigorous and refined.

BRIEF DESCRIPTION OF THE DRAWINGS

The photographs of the new plant demonstrate the overall appearance of the plant including the unique traits. The plants in the drawing are two-year-old plants growing in a full-sun research garden in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
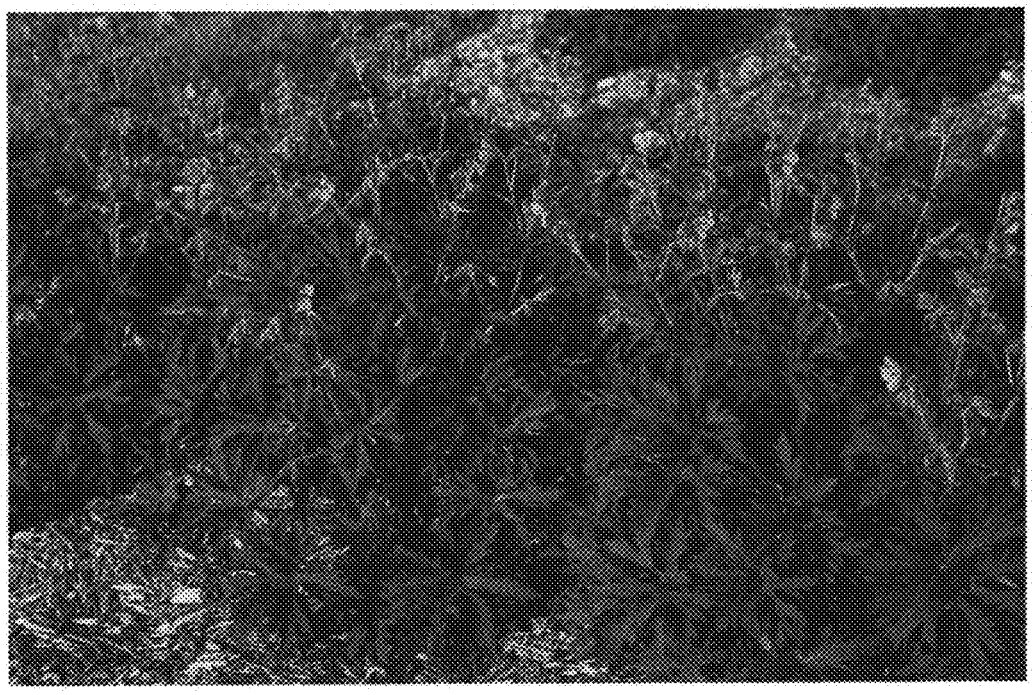
FIG. 1 shows landscape habit of plants in peak flower.
Figure 2:
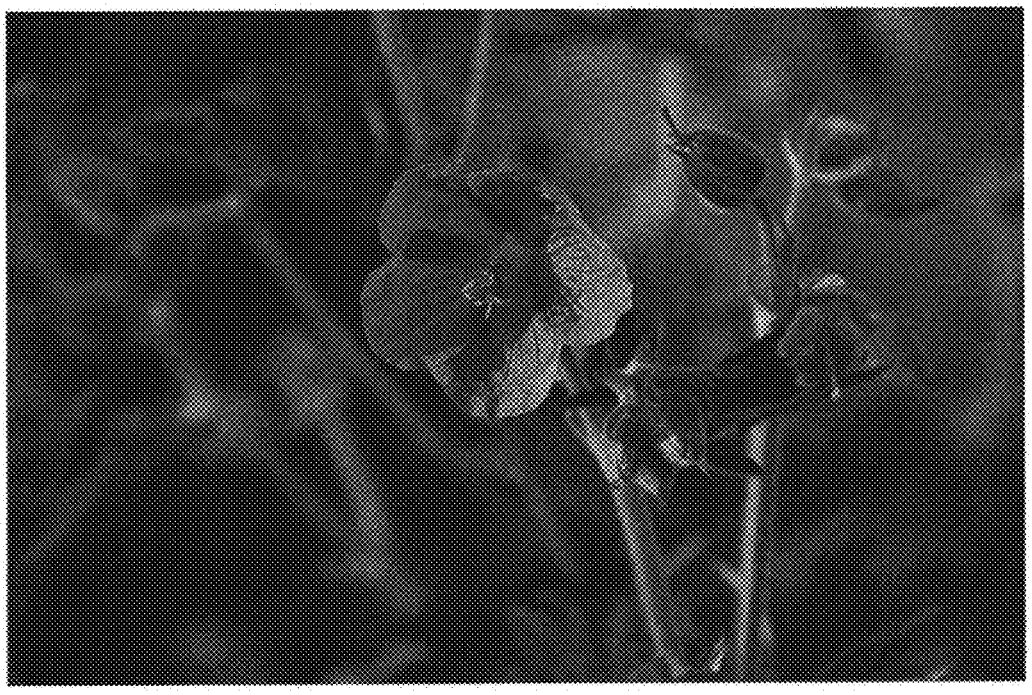
FIG. 2 shows a close-up of a flower stalk with buds and flower.

The following description is based on a two-year-old plant growing in a partially shaded greenhouse and full-sun trial garden in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 'Midnight Blues', the male or pollen parent was presumed to be 'Kashmir Blue';

Plant habit: Winter-hardy herbaceous perennial with multiple upright stems; 60.0 cm tall and 65.0 cm in diameter; with upright branched stems per plant;

Roots: Fibrous, finely branched;

Growth rate: Rapid, rooting from cutting in two weeks and finishing in three-liter container in about two and a half months;

Foliage: Opposite; palmate; rounded; deeply-cleft, pentadactylous to seven-lobed with four to six deep incisions; lobe apices acute; base hastate; margins serrate; adaxial slightly lustrous, abaxial matte; minutely puberulent adaxial, abaxial glabrous; leaf rugosity medium;

Leaf blade size: To about 12.0 cm wide and 11.5 cm long;

Leaf color: Mature adaxial between RHS NN137B and RHS 137A with undertone nearest RHS N186B in high ultraviolet light intensity; mature abaxial nearest RHS 146C; young adaxial nearest RHS 137C, young abaxial nearest RHS 146C;

Leaf quantity: Dense, about 110 per plant;

Veins: Palmate, puberulent abaxial and glabrous adaxial;

Vein color: Emerging or early spring adaxial basal midrib nearest RHS 186A and secondary and distal veins nearest RHS 187C;

Petiole: Cylindrical; to about 4.0 cm long and 2.5 mm diameter at base;

Petiole color: Nearest RHS 146C with undertone of nearest RHS 183B;

Stipule: Two per node; ovate to lanceolate; apex acute, base clasping; to about 10.0 mm long and 3.5 mm wide at base;

Stipule color: Nearest RHS 146B with undertone of nearest RHS 183B;

Peduncle: Umbel; cylindrical; stiff; puberulent; upright; branched; to about 8.0 cm long and 2.5 mm diameter at base, average about 7.0 cm tall and 2.2 mm diameter; about 27 flowers per umbel;

Inflorescence: Average size about 7.5 cm long and flowering to about 7.0 cm across;

Flowering longevity: Umbel effective for about three weeks; individual flowers about 5 to 7 days; self-cleaning;

Peduncle color: Nearest RHS 146C with blushing of nearest RHS 183A in portions getting high ultraviolet light;

Pedicel: Cylindrical, puberulent; to about 10.0 mm long and 1.0 mm diameter, average about 6.0 mm long and 0.7 mm diameter; attitude upright to outwardly;

Pedicel color: Nearest RHS 185B;

Buds one day prior to opening: Conical; acute apex and rounded base; about 12.0 mm long and 5.0 mm diameter near base;

Bud color one day prior to opening: Nearest RHS 146C with veins nearest RHS 183B;

Flower: Perfect; campanulate; single; actinomorphic; about 35.0 mm wide and 12.0 mm deep; average about 230 per flowers per plant; weakly concave;

Flower attitude: Outwardly to slightly upwardly;

Petals: Five; obovate to obcordate; rounded apex and attenuate base; entire margin; glabrous abaxial and adaxial; about 18.0 mm long and 12.0 mm wide in middle; moderately overlapping; petal veins moderately conspicuous toward center, very weakly toward margins;

Petal color: Adaxial nearest RHS 94C with contrasting palmate veins between RHS 61B and RHS 64B; abaxial nearest RHS 94D;

Calyx: Rotate; hypanthium; about 7.5 mm deep and 23.0 mm wide at apex;

Sepals: Five; ovate; acute to mucronate apex; micro-puberulent to glandular abaxial; matte adaxial; base cuneate; to about 14 mm long and 4.5 mm wide near middle;

Sepal color: Abaxial apex nearest RHS 146B with veins nearest RHS 183B adaxial nearest RHS 146D;

Androecium: Ten;

*Filaments*.—Ten, thin, glabrous; about 6.5 mm long and less than 0.3 mm diameter; color nearest RHS 186C.

*Anthers*.—Ellipsoidal, dorsifixed, longitudinal; about 2.0 mm long and about 0.5 mm across; color nearest RHS N186A.

*Pollen*.—Scarce; color nearest RHS 160C.

Gynoecium: Single; about 12.0 mm long;

*Style*.—Slightly exserted; about 9.0 mm long and about 0.5 mm diameter; color nearest RHS 186B.

*Stigma*.—Penta-fid; decurrent; about 1.5 mm long and 0.3 mm diameter; color nearest RHS 186B.

*Ovary*.—Ellipsoidal; about 2.0 mm long and 1.0 mm diameter; color nearest RHS 145A.

Fruit and seeds not observed;

Disease and pest tolerance: The new plant grows best with ample moisture and drainage in either part sun or full shade. Cold hardy from USDA zones 4 to 8. Other resistance and tolerance outside of that normal for Hardy *Geranium* is not known.

It is claimed:

1. The new and distinct Hardy *Geranium* plant named *Geranium* 'Boom Chocolatta' as herein described and illustrated.

* * * * *